US010072380B2

(12) United States Patent
Ren et al.

(10) Patent No.: US 10,072,380 B2
(45) Date of Patent: *Sep. 11, 2018

(54) DETOXIFYING AND RECYCLING OF WASHING SOLUTION USED IN PRETREATMENT OF LIGNOCELLULOSE-CONTAINING MATERIALS

(71) Applicants: Novozymes A/S, Bagsvaerd (DK); Cofco LTD, Beijing (CN)

(72) Inventors: Haiyu Ren, Beijing (CN); Hong Zhi Huang, Beijing (CN); Jie Zheng, Beijing (CN)

(73) Assignees: Novozymes Als, Bagsvaerd (DK); Cofco LTD, Beijing (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/496,928

(22) Filed: Apr. 25, 2017

(65) Prior Publication Data

US 2017/0226694 A1    Aug. 10, 2017

Related U.S. Application Data

(63) Continuation of application No. 12/203,511, filed on Sep. 3, 2008, now Pat. No. 9,695,549.

(60) Provisional application No. 60/979,893, filed on Oct. 15, 2007, provisional application No. 60/974,095, filed on Sep. 21, 2007.

(30) Foreign Application Priority Data

Sep. 3, 2007    (EP) ..................................... 07115539
Oct. 14, 2007   (EP) ..................................... 07118426

(51) Int. Cl.
  *D21C 11/00*    (2006.01)
  *D21C 9/02*     (2006.01)
  *D21C 5/00*     (2006.01)

(52) U.S. Cl.
  CPC ............ *D21C 11/005* (2013.01); *D21C 5/005* (2013.01); *D21C 9/02* (2013.01); *D21C 11/0007* (2013.01); *D21C 11/0042* (2013.01)

(58) Field of Classification Search
  CPC .. D21C 11/0042; D21C 11/005; D21C 11/007
  See application file for complete search history.

(56) References Cited

U.S. PATENT DOCUMENTS

| 3,586,537 | A |   | 6/1971  | Steiner et al. |
| 3,990,969 | A | * | 11/1976 | Broddevall ............... C02F 9/00 162/30.11 |
| 4,859,282 | A |   | 8/1989  | Chou et al. |
| 5,489,363 | A | * | 2/1996  | Marcoccia ............... D21C 3/02 162/16 |
| 6,409,841 | B1 |  | 6/2002  | Lombard |
| 2002/0195213 | A1 | | 12/2002 | Izumi et al. |
| 2007/0079944 | A1 | | 4/2007  | Amidon et al. |

FOREIGN PATENT DOCUMENTS

| EP | 0406617 A2    | 1/1991  |
| EP | 0524220 B1    | 9/1994  |
| EP | 2191061 B1    | 5/2013  |
| WO | 1996/00811 A1 | 1/1996  |
| WO | 2002/14598 A1 | 2/2002  |
| WO | 2004/041995 A1| 5/2004  |
| WO | 2004/081185 A2| 9/2004  |
| WO | 2007/146245 A2| 12/2007 |
| WO | 2009/030713 A1| 3/2009  |

OTHER PUBLICATIONS

Berlin et al, 2006, J. Biotechnol, vol. 125, pp. 198-209.
Carmona et al, 2006, Chemical Engineering Journal, vol. 117, pp. 155-160.
Carvalheiro et al, 2005, Process Biochem, vol. 40, pp. 1215-1223.
Chandel et al, 2007, Bioresource Technology, vol. 98, pp. 1947-1950.
DOW DOWEX, 2002, MWA-1 Ion Exchange Resin, pp. 1-10.
EFUNDA Saturated Steam Table, 2015, pp. 1-2.
Galbe et al, 2002, Appl Microbial Biotechnol, vol. 59, pp. 618-628.
Heald, (ED) 2002, Cameron Hydraulic Data, Flowserve Corp, Canada, pp. 1-4.
Kleinart et al, 2008, Chem Eng. Technol , vol. 31, No. 5, pp. 736-745.
Martin et al, 1988, Appl and Environmental Microbiology, pp. 1-2.
Nilvebrant et al, 2001, Applied Biochemistry and Biotechnology, pp. 91-93.
Sigma Aldrich Novozymes, 2014, pp. 1-15.
Olsson et al, 1996, Enzyme and Microbial Technology, vol. 18, pp. 312-331.
Palmqvist et al, 1996, Enzyme Microb Technol, vol. 19, pp. 470-476.
Palmqvist et al, 2000, Bioresource Technology, vol. 74, pp. 17-24.
Palmqvist et al, 2000, Bioresource Technology, vol. 74, pp. 25-33.
Rohm and Haas Company Amberlite IRA 402 CI, 2003, pp. 1.
Rohm and Haas Ion Exchange Resins, 2008, Product Data Sheet, 2 pages.
Rohm and Haas Amberlife IRN77, 2013, pp. 1-4.
Schmidt et al, 1998, Bioresource Technology, vol. 64, pp. 139-151.
Tengborg et al, 2001, Enzyme and Microbial Technology, vol. 28, pp. 835-844.
Vohra et al, 1980, Biotechnol Bioengg. vol. 22, pp. 1497-1500.
Merkmalsanalyse Anspruch 1 Novozymes EP 2191 061 B1 (Jun. 2, 2010).

\* cited by examiner

Primary Examiner — Anthony J Calandra
(74) Attorney, Agent, or Firm — Joshua L. Price; Elias Lambiris; Kelly Reynolds

(57) ABSTRACT

The invention relates to a process of detoxifying pretreated lignocellulose-containing material comprising washing the pretreated lignocellulose-containing material in a washing solution and treating the used washing solution to remove an enzyme inhibitor and/or an inhibitor of a fermenting organism before recycling the used washing solution.

19 Claims, No Drawings

DETOXIFYING AND RECYCLING OF WASHING SOLUTION USED IN PRETREATMENT OF LIGNOCELLULOSE-CONTAINING MATERIALS

CROSS-REFERENCE TO RELATED APPLICATIONS

This application is a Continuation of U.S. application Ser. No. 12/203,511 filed on Sep. 3, 2008, and published as US Patent Application Publication 2009/0056889, which application claims priority or the benefit under 35 U.S.C. 119 of EP application no. 07115539.4 filed Sep. 3, 2007 and EP application no. 07118426.1 filed Oct. 14, 2007, and U.S. provisional application no. 60/974,095 filed Sep. 21, 2007 and U.S. provisional application no. 60/979,893 filed Oct. 15, 2007, the contents of which are fully incorporated herein by reference.

TECHNICAL FIELD

The present invention relates to processes comprising detoxifying and recycling of washing solution used in pretreatment of lignocellulose-containing materials. The invention also relates to processes of producing a fermentation product from lignocellulose-containing material using a fermenting organism including a detoxification process of the invention.

BACKGROUND OF THE INVENTION

Due to the limited reserves of fossil fuels and worries about emission of greenhouse gasses there is an increasing focus on using renewable energy sources. Production of fermentation products from lignocellulose-containing material is known in the art and conventionally includes pretreatment, hydrolysis, and fermentation of the lignocellulose-containing material. Pretreatment results in the release of degradation products from the lignocellulose-containing material that may irreversibly bind and inhibit enzymes added during hydrolysis and fermentation. These compounds may also be toxic to the fermenting organism's metabolism and inhibit the performance of the fermenting organism.

Detoxification by steam stripping has been suggested but it is a cumbersome and a costly additional process step. It has also been suggested to wash the pretreated lignocellulose-containing material before hydrolysis. However, the inhibitors often have low solubility and recycling of the wash water is only possible to a very limited extend due to build-up of the inhibitors. Washing therefore requires huge amounts of water.

Consequently, there is a need for providing processes for detoxifying pretreated lignocellulose-containing material to obtain substrates suitable for hydrolysis and fermentation.

SUMMARY OF THE INVENTION

The present invention relates to processes of detoxifying pretreated lignocellulose-containing material by washing and regeneration and recycling of the used washing solution. The used washing solution is regenerated by removal of an enzyme inhibitor and/or an inhibitor of a fermenting organism. The invention also relates to processes of producing a hydrolyzate and a fermentation product from lignocellulose-containing material including a detoxification process of the invention.

In a first aspect the invention relates to a process for producing a pretreated and washed lignocellulose-containing material, the method comprising the steps of; a) subjecting a lignocellulose-containing material to a pretreatment, b) washing the pretreated lignocellulose-containing material in an washing solution, c) separating off the used washing solution to obtain a pretreated and washed lignocellulose-containing material, continuously repeating steps (a) to (c), wherein the used washing solution of step (b) is treated to remove an enzyme inhibitor and/or an inhibitor of a fermenting organism before being recycled to step (b).

In a second aspect the invention relates to a process for converting a lignocellulose-containing material into a hydrolyzate comprising mono- and oligosacchardes, the method comprising the steps of; a) subjecting a lignocellulose-containing material to a pretreatment, b) washing the pretreated lignocellulose-containing material in an washing solution, c) separating off the used washing solution to obtain a pretreated and washed lignocellulose-containing material, d) subjecting the pretreated and washed lignocellulose-containing material to a treatment resulting in at least partial hydrolysis of the cellulose and hemicellulose to obtain a hydrolyzate comprising fermentable sugars, and continuously repeating steps (a) to (d), wherein the used washing solution of step (b) is treated to remove an enzyme inhibitor and/or an inhibitor of a fermenting organism before being recycled to step (b).

In a third aspect the invention relates to a process for converting a lignocellulose-containing material into a fermentation product, the method comprising the steps of; a) subjecting a lignocellulose-containing material to a pretreatment, b) washing the pretreated lignocellulose-containing material in an washing solution, c) separating off the used washing solution to obtain a pretreated and washed lignocellulose-containing material, d) subjecting the pretreated and washed lignocellulose-containing material to a treatment resulting in at least partial hydrolysis of the cellulose and hemicellulose to obtain a hydrolyzate comprising fermentable sugars, e) contacting the hydrolyzate of step (d) with a fermenting organism to produce a fermentation product, wherein the used washing solution of step (b) is treated to remove an enzyme inhibitor and/or an inhibitor of the fermenting organism before being recycled to step (b).

The advantages of the processes include that soluble sugars (e.g. xylose, oligossachrides) produced from pretreatment can be concentrated in the washing solution; increased efficiency of the hydrolysis; increase yeast growth and/or improved fermentation of the hydrolyzates; shortening of the lag phase in fermentation; and significant reduction of washing solution consumption.

DETAILED DESCRIPTION OF THE INVENTION

In an embodiment of the first aspect the invention relates to a process for producing a pretreated and washed lignocellulose-containing material, the method comprising the steps of; a) subjecting a lignocellulose-containing material to a pretreatment, b) washing the pretreated lignocellulose-containing material in an washing solution, c) separating off the used washing solution to obtain a pretreated and washed lignocellulose-containing material, repeating steps (a) to (c), wherein the used washing solution of step (b) is treated to remove an enzyme inhibitor and/or an inhibitor of a fermenting organism before being recycled to step (b).

In an embodiment of the second aspect the invention relates to a process for converting a lignocellulose-containing material into a hydrolyzate comprising mono- and oligosacchardes, the method comprising the steps of; a) subjecting a lignocellulose-containing material to a pretreatment, b) washing the pretreated lignocellulose-containing material in an washing solution, c) separating off the used washing solution to obtain a pretreated and washed lignocellulose-containing material, d) subjecting the pretreated and washed lignocellulose-containing material to a treatment resulting in at least partial hydrolysis of the cellulose and hemicellulose to obtain a hydrolyzate comprising fermentable sugars, and repeating steps (a) to (d), wherein the used washing solution of step (b) is treated to remove an enzyme inhibitor and/or an inhibitor of a fermenting organism before being recycled to step (b).

Lignocellulose-Containing Material

The term "lignocellulose-containing materials" used herein refer to a material primarily consisting of cellulose, hemicellulose, and lignin. Lignocellulose-containing materials are often referred to as "biomass".

The structure of lignocellulose is not directly accessible to enzymatic hydrolysis. Therefore, the lignocellulose has to be pretreated, e.g., by acid hydrolysis under adequate conditions of pressure, humidity and temperature, in order to break the lignin seal and disrupt the crystalline structure of cellulose. This causes solubilization and saccharification of the hemicellulose fraction. The cellulose fraction can then be hydrolyzed e.g., enzymatically by cellulase enzymes, to convert the carbohydrate polymers into mono- and oligosaccharides, which may be fermented into a desired fermentation product, such as ethanol. Optionally the fermentation product is recovered, e.g., by distillation.

Any lignocellulose-containing material is contemplated according to the present invention. The lignocellulose-containing material may be any material containing lignocellulose. In a preferred embodiment the lignocellulose-containing material contains at least 30 wt. %, preferably at least 50 wt. %, more preferably at least 70 wt. %, even more preferably at least 90 wt. % lignocellulose. It is to be understood that the lignocellulose-containing material may also comprise other constituents such as cellulosic material, including cellulose and hemicellulose, and may also comprise other constituents such as proteinaceous material, starch, sugars, such as fermentable sugars and/or un-fermentable sugars.

Lignocellulose-containing material is generally found, for example, in the stems, leaves, hulls, husks, and cobs of plants or leaves, branches, and wood of trees. Lignocellulose-containing material can also be, but is not limited to, herbaceous material, agricultural residues, forestry residues, municipal solid wastes, waste paper, and pulp and paper mill residues. It is understood herein that lignocellulose-containing material may be in the form of plant cell wall material containing lignin, cellulose, and hemicellulose in a mixed matrix.

In a preferred embodiment the lignocellulose-containing material comprises wood chips, bagasse, paper or pulp processing waste.

Other examples include corn stover, hard wood, such as poplar and birch, soft wood such as pine wood, switch grass, cereal straw and/or husks, such as straw from rice, wheat, barley rye etc., municipal solid waste (MSW), industrial organic waste, office paper, or mixtures thereof.

In a preferred embodiment the cellulose-containing material is corn stover. In another preferred aspect, the cellulose-containing material is corn fibre.

Pretreatment

The lignocellulose-containing material may be pretreated in any suitable way. Pretreatment is carried out before hydrolysis and/or fermentation. In a preferred embodiment the pretreated material is hydrolyzed, preferably enzymatically, after the pretreatment. The goal of pretreatment is to separate and/or release cellulose; hemicellulose and/or lignin and this way improve the rate of hydrolysis. Pretreatment methods such as wet-oxidation and alkaline pretreatment targets lignin, while dilute acid and auto-hydrolysis targets hemicellulose. Steam explosion is an example of a pretreatment that targets cellulose.

According to the invention pretreatment step (a) may be a conventional pretreatment step using techniques well known in the art. In a preferred embodiment pretreatment takes place in aqueous slurry. The lignocellulose-containing material may during pretreatment be present in an amount between 10-80 wt. %, preferably between 20-70 wt. %, especially between 30-60 wt. %, such as around 50 wt. %.

The lignocellulose-containing material may according to the invention be chemically, mechanically and/or biologically pretreated before hydrolysis and/or fermentation. Mechanical treatment (often referred to as physical treatment) may be used alone or in combination with subsequent or simultaneous hydrolysis, especially enzymatic hydrolysis.

Preferably, the chemical, mechanical and/or biological pretreatment is carried out prior to the hydrolysis and/or fermentation. Alternatively, the chemical, mechanical and/or biological pretreatment may be carried out simultaneously with hydrolysis, such as simultaneously with addition of one or more cellulase enzymes, or other enzyme activities mentioned below, to release, e.g., fermentable sugars, such as glucose and/or maltose.

The term "chemical treatment" refers to any chemical pretreatment which promotes the separation and/or release of cellulose, hemicellulose and/or lignin. Examples of suitable chemical pretreatments include treatment with; for example, dilute acid, lime, alkaline, organic solvent, ammonia, sulfur dioxide, carbon dioxide. Further, wet oxidation and pH-controlled hydrothermolysis are also considered chemical pretreatment.

In a preferred embodiment the chemical pretreatment is acid treatment, more preferably, a continuous dilute and/or mild acid treatment, such as, treatment with sulfuric acid, or another organic acid, such as acetic acid, citric acid, tartaric acid, succinic acid, hydrogen chloride or mixtures thereof. Other acids may also be used. Mild acid treatment means that the treatment pH lies in the range from 1-5, preferably pH 1-3. In a specific embodiment the acid concentration is in the range from 0.1 to 2.0 wt. % acid, preferably sulphuric acid. The acid may be contacted with the lignocellulose-containing material and the mixture may be held at a temperature in the range of 160-220° C., such as 165-195° C., for periods ranging, e.g., 1-60 minutes, such as 2-30 minutes or 3-12 minutes. Addition of strong acids, such as sulphuric acid, may be applied to remove hemicellulose. This enhances the digestibility of cellulose.

Other techniques are also contemplated. Cellulose solvent treatment has been shown to convert about 90% of cellulose to glucose. It has also been shown that enzymatic hydrolysis could be greatly enhanced when the lignocellulose structure is disrupted. Alkaline $H_2O_2$, ozone, organosolv (uses Lewis acids, $FeCl_3$, $(Al)_2SO_4$ in aqueous alcohols), glycerol, dioxane, phenol, or ethylene glycol are among solvents known to disrupt cellulose structure and promote hydrolysis (Mosier et al., 2005, Bioresource Technology 96: 673-686).

Alkaline chemical pretreatment with base, e.g., NaOH, $Na_2CO_3$ and/or ammonia or the like, is also contemplated according to the invention. Pretreatments method using ammonia is described in, e.g., WO 2006/110891, WO 2006/110899, WO 2006/110900, WO 2006/110901 (which are hereby incorporated by reference).

Wet oxidation techniques involve use of oxidizing agents, such as: sulphite based oxidizing agents or the like. Examples of solvent pretreatments include treatment with DMSO (Dimethyl Sulfoxide) or the like. Chemical pretreatment is generally carried out for 1 to 60 minutes, such as from 5 to 30 minutes, but may be carried out for shorter or longer periods of time dependent on the material to be pretreated.

Other examples of suitable pretreatment methods are described by Schell et al., 2003, Appl. Biochem and Biotechn. 105-108: 69-85, Mosier et al., 2005, Bioresource Technology 96" 673-686, Ahring et al. in WO 2006/032282 and WO 2001/60752, Foody et al. in WO 2006/034590, and Ballesteros et al. in U.S. Application Publication No. 2002/0164730, which references are hereby all incorporated by reference.

The term "mechanical pretreatment" refers to any mechanical (or physical) treatment which promotes the separation and/or release of cellulose, hemicellulose and/or lignin from lignocellulose-containing material. For example, mechanical pretreatment includes various types of milling, irradiation, steaming/steam explosion, wet oxidation, and other hydrothermal treatments.

Mechanical pretreatment includes comminution (mechanical reduction of the size). Comminution includes dry milling, wet milling and vibratory ball milling. Mechanical pretreatment may involve high pressure and/or high temperature (steam explosion). In an embodiment of the invention high pressure means pressure in the range from 300 to 600 psi, preferably 400 to 500 psi, such as around 450 psi. In an embodiment of the invention high temperature means temperatures in the range from about 100 to 300° C., preferably from about 140 to 235° C. In a preferred embodiment mechanical pretreatment is a batch-process, steam gun hydrolyzer system which uses high pressure and high temperature as defined above. A Sunds Hydrolyzer (available from Sunds Defibrator AB (Sweden) may be used for this.

In a preferred embodiment both chemical and mechanical pretreatments are carried out. For instance, the pretreatment step may involve dilute or mild acid treatment and high temperature and/or pressure treatment. The chemical and mechanical pretreatment may be carried out sequentially or simultaneously, as desired.

Accordingly, in a preferred embodiment, the lignocellulose-containing material is subjected to both chemical and mechanical pretreatment to promote the separation and/or release of cellulose, hemicellulose and/or lignin.

In a preferred embodiment a mechanical pretreatment is carried out before a stream explosion pretreatment.

In a preferred embodiment the pretreatment is carried out as a dilute and/or mild acid steam explosion step. In another preferred embodiment pretreatment is carried out as an ammonia fiber explosion step (or AFEX pretreatment step).

As used in the present invention the term "biological pretreatment" refers to any biological pretreatment which promotes the separation and/or release of cellulose, hemicellulose, and/or lignin from the lignocellulose-containing material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of lignocellulosic biomass, *Adv. Appl. Microbiol.* 39: 295-333; McMillan, 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech.* 18: 312-331; and Vallander, L., and Eriksson, K.-E. L., 1990, Production of ethanol from lignocellulosic materials: State of the art, *Adv. Biochem. Eng./Biotechnol.* 42: 63-95).

Process of Detoxifying Pretreated Lignocellulose-Containing Material

When lignocellulose-containing material is pretreated, degradation products that are toxic and/or inhibitory to enzymes and fermenting organisms are produced. These compounds severely decrease both the hydrolysis and fermentation rate.

Detoxifying of pretreated lignocellulose-containing material in order to remove inhibitors of enzymes and/or a fermenting organism will improve the enzymatic hydrolysis and/or improve performance of the fermenting organism during fermentation. In other words, detoxification in accordance with the invention results in a shorter "lignocellulose-containing material to fermentation product" process time.

The inhibitors are lignocellulose degradation products including lignin degradation products, cellulose degradation products and hemicellulose degradation products. The lignin degradation products may be phenolic in nature. The hemicellulose degradation products include furans from sugars (such as hexoses and/or pentoses), including xylose, mannose, galactose, rhamanose, and arabinose. Examples of hemicelluloses include xylan, galactoglucomannan, arabinogalactan, arabinoglucuronoxylan, glucuronoxylan, and derivatives and combinations thereof. Examples of inhibitory compounds, i.e., pretreated lignocellulose degradation products, include 4-OH benzyl alcohol, 4-OH benzaldehyde, 4-OH benzoic acid, trimethyl benzaldehyde, 2-furoic acid, coumaric acid, ferulic acid, phenol, guaiacol, veratrole, pyrogallollol, pyrogallol mono methyl ether, vanillyl alcohol, vanillin, isovanillin, vanillic acid, isovanillic acid, homovanillic acid, veratryl alcohol, veratraldehyde, veratric acid, 2-O-methyl gallic acid, syringyl alcohol, syringaldehyde, syringic acid, trimethyl gallic acid, homocatechol, ethyl vanillin, creosol, p-methyl anisol, anisaldehyde, anisic acid, furfural, hydroxymethylfurfural, 5-hydroxymethylfurfural, formic acid, acetic acid, levulinic acid, cinnamic acid, coniferyl aldehyde, isoeugenol, hydroquinone, eugenol or combinations thereof.

According to the first, second and third aspects to the present invention compounds toxic and/or inhibitory to enzymes and/or a fermenting organism are removed from the pretreated lignocellulose-containing material by washing with a washing solution. The washing solution is preferably an aqueous washing solution. The washing solution may be a substantially pure solution of water, or water with a significant amount of additives, e.g. such as a detergent and/or an organic solvent to improve the extraction and/or solubility of the compounds toxic and/or inhibitory to enzymes and/or a fermenting organism. A suitable organic solvent is ethanol or methanol.

The washing solution is preferably applied at a temperature of 5 to 70° C., preferably of 10 to 50° C., and more preferably 15 to 30° C., e.g., at a temperature from 20 to 25° C.

The washing step ends when the used washing solution is separated from the washed PCS. The separation of the used washing solution may be achieved by any suitable method including but not limited to draining, filtration, centrifugation and pressing.

According to the first, second and third aspects to the present invention the used washing solution is treated to remove an enzyme inhibitor and/or an inhibitor of the fermenting organism before being recycled to the washing step. The treatment regenerates the used washing solution in order to create a usable washing solution. In a preferred embodiment the used washing solution is treated by contacting it with a resin or a combination of resins. The combination of resins may be applied as a mixture of two or more resins and/or it may be two or more resins applied one after the other. The resin may be a resin with a polar, a weakly polar or non-polar functional group. The resin may be a strongly acidic cation exchanger, a weakly acidic cation exchanger, a strongly basic anion exchanger, or a weakly basic anion exchanger. Preferred functional groups include —$SO_3$, —COOH, —$N+(CH_3)_3$, —$N(CH_3)_2$ and —$NH_2$. The resin may also be a charcoal resin. A suitable resin may be selected from the group consisting of resins D380, H103, AB-8, D101, NKA, NKA9, D301T, D296R and D401, which are obtainable from NanKai Chemical Industry, Japan. Particularly preferred resins are D380 and H103. In a preferred embodiment the used washing solution is treated by contacting it with activated charcoal.

In a preferred embodiment the used washing solution is passed through a column comprising the resin and/or activated charcoal.

Hydrolysis

Before and/or simultaneously with fermentation the pretreated and washed lignocellulose-containing material may be hydrolyzed to break down cellulose and hemicellulose into sugars and/or oligosaccharides.

The dry solids content during hydrolysis may be in the range from 5-50 wt. %, preferably 10-40 wt. %, preferably 20-30 wt. %. Hydrolysis may in a preferred embodiment be carried out as a fed batch process where the pretreated lignocellulose-containing material (substrate) is fed gradually to an, e.g., enzyme containing hydrolysis solution. The pretreated lignocellulose-containing material may be supplied to the enzyme containing hydrolysis solution either in one or more distinct batches, as one or more distinct continuous flows or as a combination of one or more distinct batches and one or more distinct continuous flows.

In a preferred embodiment hydrolysis is carried out enzymatically. According to the invention the pretreated lignocellulose-containing material may be hydrolyzed by one or more hydrolases (class EC 3 according to Enzyme Nomenclature), preferably one or more carbohydrases selected from the group consisting of cellulase, hemicellulase, amylase, such as alpha-amylase, carbohydrate-generating enzyme, such as glucoamylase, esterase, such as lipase, or protease. Alpha-amylase, glucoamylase and/or the like may be present during hydrolysis and/or fermentation as the lignocellulose-containing material may include some starch.

The enzyme(s) used for hydrolysis is(are) capable of directly or indirectly converting carbohydrate polymers into fermentable sugars which can be fermented into a desired fermentation product, such as ethanol.

In a preferred embodiment the carbohydrase has cellulase enzyme activity. Suitable carbohydrases are described in the "Enzymes"-section below.

Hemicellulose polymers can be broken down by hemicellulases and/or acid hydrolysis to release its five and six carbon sugar components. The six carbon sugars (hexoses), such as glucose, galactose, arabinose, and mannose, can readily be fermented to, e.g., ethanol, acetone, butanol, glycerol, citric acid, fumaric acid etc. by suitable fermenting organisms including yeast. Preferred for ethanol fermentation is yeast of the species *Saccharomyces cerevisiae*, preferably strains which are resistant towards high levels of ethanol, i.e., up to, e.g., about 10, 12 or 15 vol. % ethanol or more, such as 20 vol. % ethanol.

In a preferred embodiment the pretreated lignocellulose-containing material is hydrolyzed using a hemicellulase, preferably a xylanase, esterase, cellobiase, or combination thereof.

Hydrolysis may also be carried out in the presence of a combination of hemicellulases and/or cellulases, and optionally one or more of the other enzyme activities mentioned in the "Enzyme" section below.

Enzymatic treatment may be carried out in a suitable aqueous environment under conditions which can readily be determined by one skilled in the art. In a preferred embodiment hydrolysis is carried out at suitable, preferably optimal conditions for the enzyme(s) in question.

Suitable process time, temperature and pH conditions can readily be determined by one skilled in the art present invention. Preferably, hydrolysis is carried out at a temperature between 25° C. and 70° C., preferably between 40° C. and 60° C., especially around 50° C. The process is preferably carried out at a pH in the range from 3-8, preferably pH 4-6, especially around pH 5.

Preferably, hydrolysis is carried out for between 12 and 144 hours, preferable 16 to 120 hours, more preferably between 24 and 96 hours, such as between 32 and 48 hours.

According to the invention hydrolysis in step (c) and fermentation in step (d) may be carried out simultaneously (SHHF process) or sequentially (SHF process).

Fermentation

According to the invention the pretreated (and hydrolyzed) lignocellulose-containing material is fermented by at least one fermenting organism capable of fermenting fermentable sugars, such as glucose, xylose, mannose, and galactose directly or indirectly into a desired fermentation product.

The fermentation is preferably ongoing for between 8 to 96 hours, preferably 12 to 72, more preferable from 24 to 48 hours.

In an embodiment the fermentation is carried out at a temperature between 20 to 40° C., preferably 26 to 34° C., in particular around 32° C. In an embodiment the pH is from pH 3 to 6, preferably around pH 4 to 5.

Contemplated according to the invention is simultaneous hydrolysis and fermentation (SHF). In an embodiment there is no separate holding stage for the hydrolysis, meaning that the hydrolysing enzyme(s) and the fermenting organism are added together. When the fermentation (e.g., ethanol fermentation using *Saccharomyces* yeast) is performed simultaneous with hydrolysis the temperature is preferably between 26° C. and 35° C., more preferably between 30° C. and 34° C., such as around 32° C. A temperature program comprising at least two holding stages at different temperatures may be applied according to the invention.

During washing of the pretreated lignocellulose-containing material dissolved sugars may accumulate in the recycled aqueous washing solution. These sugars can be separated out and fermented with a suitable fermenting organism. As the dissolved sugars will comprise C5 sugars from the degradation of the hemicellulose, such as xylose, a preferred fermenting organism is able to convert C5 sugars into a desired fermentation product.

The process of the invention may be performed as a batch, fed-batch or as a continuous process. Preferably the fermentation step is performed as a continuous fermentation.

Recovery

Subsequent to fermentation the fermentation product may be separated from the fermentation broth. The broth may be distilled to extract the fermentation product or the fermentation product may be extracted from the fermentation broth by micro or membrane filtration techniques. Alternatively the fermentation product may be recovered by stripping. Recovery methods are well known in the art.

Fermentation Products

The process of the invention may be used for producing any fermentation product. Especially contemplated fermentation products include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones.

Also contemplated products include consumable alcohol industry products, e.g., beer and wine; dairy industry products, e.g., fermented dairy products; leather industry products and tobacco industry products. In a preferred embodiment the fermentation product is an alcohol, especially ethanol. The fermentation product, such as ethanol, obtained according to the invention, may preferably be fuel alcohol/ethanol. However, in the case of ethanol it may also be used as potable ethanol.

Fermenting Organisms

The term "fermenting organism" refers to any organism, including bacterial and fungal organisms, suitable for producing a desired fermentation product. Especially suitable fermenting organisms according to the invention are able to ferment, i.e., convert, sugars, such as glucose, directly or indirectly into the desired fermentation product. Also suitable are fermenting organisms capable of converting C5 sugars such as xylose into a desired fermentation product. Examples of fermenting organisms include fungal organisms, especially yeast. Preferred yeast includes strains of *Saccharomyces* spp., in particular a strain of *Saccharomyces cerevisiae* or *Saccharomyces uvarum*; a strain of *Pichia*, preferably *Pichia stipitis*, such as *Pichia stipitis* CBS 5773; a strain of *Candida*, in particular a strain of *Candida utilis*, *Candida diddensii*, or *Candida boidinii*. Other contemplated yeast includes strains of *Zymomonas; Hansenula*, in particular *H. anomala; Klyveromyces*, in particular *K. fragilis*; and *Schizosaccharomyces*, in particular *S. pombe*.

Commercially available yeast includes, e.g., ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties). ANQI YEAST (available from Anqi yeast (CHIFENG) CO., LTD, China).

Enzymes

Even though not specifically mentioned in context of a process of the invention, it is to be understood that the enzymes (as well as other compounds) are used in an "effective amount".

Cellulases

The term "cellulases" as used herein are understood as comprising the cellobiohydrolases (EC 3.2.1.91), e.g., cellobiohydrolase I and cellobiohydrolase II, as well as the endo-glucanases (EC 3.2.1.4) and beta-glucosidases (EC 3.2.1.21).

In order to be efficient, the digestion of cellulose and hemicellulose requires several types of enzymes acting cooperatively. At least three categories of enzymes are necessary to convert cellulose into fermentable sugars: endoglucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases are the key enzymes for the degradation of native crystalline cellulose. The term "cellobiohydrolase I" is defined herein as a cellulose 1,4-beta-cellobiosidase (also referred to as Exo-glucanase, Exo-cellobiohydrolase or 1,4-beta-cellobiohydrolase) activity, as defined in the enzyme class EC 3.2.1.91, which catalyzes the hydrolysis of 1,4-beta-D-glucosidic linkages in cellulose and cellotetraose, by the release of cellobiose from the non-reducing ends of the chains. The definition of the term "cellobiohydrolase II activity" is identical, except that cellobiohydrolase II attacks from the reducing ends of the chains.

Endoglucanases (EC No. 3.2.1.4) catalyzes endo hydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans and other plant material containing cellulosic parts. The authorized name is endo-1,4-beta-D-glucan 4-glucano hydrolase, but the abbreviated term endoglucanase is used in the present specification.

The cellulases may comprise a carbohydrate-binding module (CBM) which enhances the binding of the enzyme to a cellulose-containing fiber and increases the efficacy of the catalytic active part of the enzyme. A CBM is defined as contiguous amino acid sequence within a carbohydrate-active enzyme with a discreet fold having carbohydrate-binding activity. For further information of CBMs see the CAZy internet server (Supra) or Tomme et al., (1995) in Enzymatic Degradation of Insoluble Polysaccharides (Saddler, J. N. & Penner, M., eds.), Cellulose-binding domains: classification and properties. pp. 142-163, American Chemical Society, Washington.

The cellulase activity may, in a preferred embodiment, be derived from a fungal source, such as a strain of the genus *Trichoderma*, preferably a strain of *Trichoderma reesei*; a strain of the genus *Humicola*, such as a strain of *Humicola insolens*; or a strain of *Chrysosporium*, preferably a strain of *Chrysosporium lucknowense*.

In a preferred embodiment the cellulases may a preparation as defined in co-pending application U.S. patent application No. 60/941,251, which is hereby incorporated by reference. In a preferred embodiment the cellulase preparation comprising a polypeptide having cellulolytic enhancing activity (GH61A), preferably the one disclosed in WO 2005/074656. The cellulase preparation may further comprise a beta-glucosidase, such as the fusion protein disclosed in U.S. patent application No. 60/832,511. In an embodiment the cellulase preparation also comprises a CBH II, preferably *Thielavia terrestris* cellobiohydrolase II CEL6A. In an embodiment the cellulase preparation also comprises a cellulase enzymes preparation, preferably the one derived from *Trichoderma reesei*. In a preferred embodiment the cellulase preparation is Cellulase preparation A used in Example 1 disclosed in co-pending U.S. patent application No. 60/941,251.

In an embodiment the cellulase is the commercially available product CELLUCLAST® 1.5 L or CELLUZYME™ (Novozymes A/S, Denmark).

A cellulase may be added for hydrolyzing the pretreated lignocellulose-containing material. The cellulase may be dosed in the range from 0.1-100 FPU per gram dry solids (DS), preferably 0.5-50 FPU per gram DS, especially 1-20 FPU per gram DS.

Hemicellulases

Hemicellulose can be broken down by hemicellulases and/or acid hydrolysis to release its five and six carbon sugar components. In an embodiment of the invention the lignocellulose derived material may be treated with one or more hemicellulase.

Any hemicellulase suitable for use in hydrolyzing hemicellulose may be used. Preferred hemicellulases include xylanases, arabinofuranosidases, acetyl xylan esterase, feruloyl esterase, glucuronidases, endo-galactanase, mannases, endo or exo arabinases, exo-galactanases, and mixtures of two or more thereof. Preferably, the hemicellulase for use in the present invention is an exo-acting hemicellulase, and more preferably, the hemicellulase is an exo-acting hemicellulase which has the ability to hydrolyze hemicellulose under acidic conditions of below pH 7, preferably pH 3-7. An example of hemicellulase suitable for use in the present invention includes VISCOZYME™ (available from Novozymes A/S, Denmark).

Arabinofuranosidase (EC 3.2.1.55) catalyzes the hydrolysis of terminal non-reducing alpha-L-arabinofuranoside residues in alpha-L-arabinosides.

Galactanase (EC 3.2.1.89), arabinogalactan endo-1,4-beta-galactosidase, catalyzes the endohydrolysis of 1,4-D-galactosidic linkages in arabinogalactans.

Pectinase (EC 3.2.1.15) catalyzes the hydrolysis of 1,4-alpha-D-galactosiduronic linkages in pectate and other galacturonans.

Xyloglucanase catalyzes the hydrolysis of xyloglucan.

The hemicellulase may be added in an amount effective to hydrolyze hemicellulose, such as, in amounts from about 0.001 to 0.5 wt. % of dry solids (DS), more preferably from about 0.05 to 0.5 wt. % of DS.

Alpha-Amylases

According to the invention an alpha-amylase may be used. In a preferred embodiment the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention the bacterial alpha-amylase is preferably derived from the genus *Bacillus*.

In a preferred embodiment the *Bacillus* alpha-amylase is derived from a strain of *B. licheniformis*, *B. amyloliquefaciens*, *B. subtilis* or *B. stearothermophilus*, but may also be derived from other *Bacillus* sp. Specific examples of contemplated alpha-amylases include the *Bacillus licheniformis* alpha-amylase shown in SEQ ID NO: 4 in WO 99/19467, the *Bacillus amyloliquefaciens* alpha-amylase SEQ ID NO: 5 in WO 99/19467 and the *Bacillus stearothermophilus* alpha-amylase shown in SEQ ID NO: 3 in WO 99/19467 (all sequences hereby incorporated by reference). In an embodiment of the invention the alpha-amylase may be an enzyme having a degree of identity of at least 60%, preferably at least 70%, more preferred at least 80%, even more preferred at least 90%, such as at least 95%, at least 96%, at least 97%, at least 98% or at least 99% to any of the sequences shown in SEQ ID NO: 1, 2 or 3, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 96/23873—see e.g., page 20, lines 1-10 (hereby incorporated by reference), preferably corresponding to delta(181-182) compared to the wild-type BSG alpha-amylase amino acid sequence set forth in SEQ ID NO: 3 disclosed in WO 99/19467 or deletion of amino acids R179 and G180 using SEQ ID NO: 3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta (181-182) and further comprise a N193F substitution (also denoted I181*+G182*+N193F) compared to the wild-type BSG alpha-amylase amino acid sequence set forth in SEQ ID NO: 3 disclosed in WO 99/19467.

Bacterial Hybrid Alpha-Amylases

A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with one or more, especially all, of the following substitution: G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

Fungal Alpha-Amylases

Fungal alpha-amylases include alpha-amylases derived from a strain of the genus *Aspergillus*, such as, *Aspergillus oryzae*, *Aspergillus niger* and *Aspergillis kawachii* alpha-amylases.

A preferred acidic fungal alpha-amylase is a Fungamyl-like alpha-amylase which is derived from a strain of *Aspergillus oryzae*. According to the present invention, the term "Fungamyl-like alpha-amylase" indicates an alpha-amylase which exhibits a high identity, i.e. at least 70%, at least 75%, at least 80%, at least 85% at least 90%, at least 95%, at least 96%, at least 97%, at least 98%, at least 99% or even 100% identity to the mature part of the amino acid sequence shown in SEQ ID NO: 10 in WO 96/23874.

Another preferred acidic alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in WO 89/01969 (Example 3). A commercially available acid fungal alpha-amylase derived from *Aspergillus niger* is SP288 (available from Novozymes A/S, Denmark).

Other contemplated wild-type alpha-amylases include those derived from a strain of the genera *Rhizomucor* and *Meripilus*, preferably a strain of *Rhizomucor pusillus* (WO 2004/055178 incorporated by reference) or *Meripilus giganteus*.

In a preferred embodiment the alpha-amylase is derived from *Aspergillus kawachii* and disclosed by Kaneko et al., 1996, J. Ferment. Bioeng. 81: 292-298, "Molecular-cloning and determination of the nucleotide-sequence of a gene encoding an acid-stable alpha-amylase from *Aspergillus kawachii*"; and further as EMBL:#AB008370.

The fungal alpha-amylase may also be a wild-type enzyme comprising a starch-binding domain (SBD) and an alpha-amylase catalytic domain (i.e., none-hybrid), or a variant thereof. In an embodiment the wild-type alpha-amylase is derived from a strain of *Aspergillus kawachii*.

Fungal Hybrid Alpha-Amylases

In a preferred embodiment the fungal acid alpha-amylase is a hybrid alpha-amylase. Preferred examples of fungal hybrid alpha-amylases include the ones disclosed in WO 2005/003311 or U.S. Application Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. patent application No. 60/638,614, including Fungamyl variant with catalytic domain JA118 and *Athelia rolfsii* SBD (SEQ ID NO: 100 in U.S. patent application 60/638,614), *Rhizomucor pusillus* alpha-amylase with *Athelia rolfsii* AMG linker and SBD (SEQ ID NO: 101 in U.S. patent application No. 60/638,614), *Rhizomucor pusillus* alpha-amylase with *Aspergillus niger* glucoamylase linker and SBD (which is disclosed in Table 5 as a combination of amino acid sequences SEQ ID NO: 20 SEQ ID NO: 72 and SEQ ID NO:96 in U.S. patent application Ser. No. 11/316,535) or as V039 in Table 5 in WO 2006/069290, and *Meripilus giganteus* alpha-amylase with *Athelia rolfsii* glucoamylase linker and SBD (SEQ ID NO: 102 in U.S. patent application No. 60/638,614). Other specifically contemplated hybrid alpha-amylases are any of the ones listed in Tables 3, 4, 5, and 6 in Example 4 in U.S. patent application Ser. No. 11/316,535 and WO 2006/069290 (hereby incorporated by reference).

Other specific examples of contemplated hybrid alpha-amylases include those disclosed in U.S. Application Publication no. 2005/0054071, including those disclosed in Table 3 on page 15, such as *Aspergillus niger* alpha-amylase with *Aspergillus kawachii* linker and starch binding domain.

Contemplated are also alpha-amylases which exhibit a high identity to any of above mention alpha-amylases, i.e., at least 70%, at least 75%, at least 80%, at least 85% at least 90%, at least 95%, at least 96%, at least 97%, at least 98%, at least 99% or even 100% identity to the mature enzyme sequences.

An acid alpha-amylases may according to the invention be added in an amount of 0.1 to 10 AFAU/g DS, preferably 0.10 to 5 AFAU/g DS, especially 0.3 to 2 AFAU/g DS.

Commercial Alpha-Amylase Products

Preferred commercial compositions comprising alpha-amylase include MYCOLASE from DSM, BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, and SPEZYME™ DELTA AA (Genencor Int.), and the acid fungal alpha-amylase sold under the trade name SP288 (available from Novozymes A/S, Denmark).

Carbohydrate-Source Generating Enzymes

The term "carbohydrate-source generating enzyme" includes glucoamylase (being glucose generators), beta-amylase and maltogenic amylase (being maltose generators). A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Especially contemplated mixtures are mixtures of at least a glucoamylase and an alpha-amylase, especially an acid amylase, even more preferred an acid fungal alpha-amylase. The ratio between acidic fungal alpha-amylase activity (AFAU) per glucoamylase activity (AGU) (AFAU per AGU) may in an embodiment of the invention be at least 0.1, in particular at least 0.16, such as in the range from 0.12 to 0.50 or more.

Glucoamylases

A glucoamylase used according to the invention may be derived from any suitable source, e.g., derived from a microorganism or a plant. Preferred glucoamylases are of fungal or bacterial origin, selected from the group consisting of *Aspergillus* glucoamylases, in particular *A. niger* G1 or G2 glucoamylase (Boel et al., 1984, EMBO J. 3 (5): p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (Agric. Biol. Chem., 1991, 55(4): 941-949), or variants or fragments thereof. Other *Aspergillus* glucoamylase variants include variants with enhanced thermal stability: G137A and G139A (Chen et al., 1996, Prot. Eng. 9: 499-505); D257E and D293E/Q (Chen et al., 1995, Prot. Eng. 8: 575-582); N182 (Chen et al., 1994, Biochem. J. 301, 275-281); disulphide bonds, A246C (Fierobe et al., 1996, Biochemistry, 35: 8698-8704; and introduction of Pro residues in position A435 and S436 (Li et al., 1997, Protein Eng. 10: 1199-1204.

Other glucoamylases include *Athelia rolfsii* (previously denoted *Corticium rolfsii*) glucoamylase (see U.S. Pat. No. 4,727,026 and (Nagasaka et al., 1998, "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti*, *Talaromyces thermophilus* (U.S. Pat. No. 4,587,215).

Bacterial glucoamylases contemplated include glucoamylases from the genus *Clostridium*, in particular *C. thermoamylolyticum* (EP 135,138), and *C. thermohydrosulfuricum*

(WO 86/01831) and *Trametes cingulata* disclosed in WO 2006/069289 (which is hereby incorporated by reference).

Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference.).

Contemplated are also glucoamylases which exhibit a high identity to any of above mention glucoamylases, i.e., at least 70%, at least 75%, at least 80%, at least 85% at least 90%, at least 95%, at least 96%, at least 97%, at least 98%, at least 99% or even 100% identity to the mature enzymes sequences.

Commercially available compositions comprising glucoamylase include AMG 200 L; AMG 300 L; SAN™ SUPER, SAN™ EXTRA L, SPIRIZYME™ PLUS, SPIRIZYME™ FUEL, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylases may in an embodiment be added in an amount of 0.02-20 AGU/g DS, preferably 0.1-10 AGU/g DS, especially between 1-5 AGU/g DS, such as 0.5 AGU/g DS.

Maltogenic Amylases

The amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may in a preferred embodiment be added in an amount of 0.05-5 mg total protein/gram DS or 0.05-5 MANU/g DS.

Proteases

The protease may according to the invention be any protease. In a preferred embodiment the protease is an acid protease of microbial origin, preferably of fungal or bacterial origin.

Suitable proteases include microbial proteases, such as fungal and bacterial proteases. Preferred proteases are acidic proteases, i.e., proteases characterized by the ability to hydrolyze proteins under acidic conditions below pH 7.

Contemplated acid fungal proteases include fungal proteases derived from *Aspergillus, Mucor, Rhizopus, Candida, Coriolus, Endothia, Enthomophtra, Irpex, Penicillium, Scierotium* and *Torulopsis*. Especially contemplated are proteases derived from *Aspergillus niger* (see, e.g., Koaze et al., 1964, Agr. Biol. Chem. Japan 28: 216), *Aspergillus saitoi* (see, e.g., Yoshida, 1954, J. Agr. Chem. Soc. Japan 28: 66), *Aspergillus awamori* (Hayashida et al., 1977, Agric. Biol. Chem. 42(5): 927-933, *Aspergillus aculeatus* (WO 95/02044), or *Aspergillus oryzae*, such as the pepA protease; and acidic proteases from *Mucor pusillus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No. P06832. Also contemplated are the proteases having at least 90% identity to amino acid sequence obtainable at Swissprot as Accession No. P06832 such as at least 92%, at least 95%, at least 96%, at least 97%, at least 98%, or particularly at least 99% identity.

Further contemplated are the proteases having at least 90% identity to amino acid sequence disclosed as SEQ ID NO: 1 in WO 2003/048353 such as at 92%, at least 95%, at least 96%, at least 97%, at least 98%, or particularly at least 99% identity.

Also contemplated are papain-like proteases such as proteases within E.C. 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

Proteases may be added in the amounts of 0.1-1000 AU/kg dm, preferably 1-100 AU/kg DS and most preferably 5-25 AU/kg DS.

Materials & Methods

Enzymes:

Cellulase preparation A: Cellulolytic composition comprising a polypeptide having cellulolytic enhancing activity (GH61A) disclosed in WO 2005/074656; an *Aspergillus oryzae* beta-glucosidase (in the fusion protein disclosed in U.S. application No. 60/832,511), and a cellulolytic enzyme preparation derived from *Trichoderma reesei*. Cellulase preparation A is disclosed in co-pending U.S. patent application No. 60/941,251.

Determination of Identity

The relatedness between two amino acid sequences or between two nucleotide sequences is described by the parameter "identity".

The degree of identity between two amino acid sequences may be determined by the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

The degree of identity between two nucleotide sequences may be determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

EXAMPLES

Example 1

Corn stover was pretreated using steam explosion at 205° C. for 5.4 min. Pretreated corn stover (PCS) 666 g with DS of 38% was mixed with 2 L aqueous washing solution (water to PCS weight ratio 3:1) and incubated with stirring for 30 minutes at room temperature. The used washing solution from the PCS was squeezed out through 8 layers cheese cloth and filtered through 32 layers cheese cloth. About 1800 ml used washing solution was obtained. The used washing solution was treated by incubation with 500 g of resin D380 (average used washing solution to resin ratio approximately 3:1) in a beaker for 60 minutes with shaking. D380 is a macroporous weakly basic anion exchanger. Prior to use the resin was washed in a conventional way. The treated washing solution was recycled to wash a new batch of 600 g unwashed PCS, followed by separation, filtration, and resin treatment and recycling for yet a washing. This washing solution was recycled 5 times to wash 5 batches of unwashed PCS. As control treatment used washing solution was recycled without resin treatment 5 times. Approximately 90% of the washing solution was recovered from each wash. The size of the subsequent PCS portion was correspondingly decreased to maintain constant water to PCS weight ratio.

The washed PCS was subjected to a fed-batch hydrolysis process starting with a batch hydrolysis comprising 110 g of water and substrate with an initial dry solids concentration of 12%. Pennicilin was added for controlling bacterial contamination. Cellulase composition A was utilized for enzymatic hydrolysis in a concentration of 138 EGU/g cellulose. Washed PCS was added in 3 additional loadings to a final weight of 350 grams and a final dry solids concentration of 25%. The fed-batch hydrolysis process was performed at 50° C. and pH 4.8. Unless specified the total hydrolysis time was 96 hours. The results are shown in table 1.

The hydrolyzates were pitched with Anqi dry yeast (0.5% w/w), 0.25% urea and fermented at 32° C. for 6 days. The results are shown in table 2.

TABLE 1

Hydrolysis of washed PCS using recycled water with and without resin treatment. Glucose yield from cellulose (%).

| | |
|---|---|
| Cycle No. 1 | 62.14 |
| Cycle No. 5 with resin | 53.05 |
| Cycle No. 5 without resin* | 44.99 |

*Sampled after 120 hours of hydrolysis

TABLE 2

Fermentation of hydrolyzates of PCS washed in recycled water with or without resin treatment of wash water. Ethanol production (g/L)

| | Day 1 | Day 2 | Day 3 | Day 4 | Day 5 | Day 6 |
|---|---|---|---|---|---|---|
| Cycle No. 1 | 16.96 | 27.04 | 37.97 | 39.29 | 39.98 | 40.68 |
| Cycle No. 5 with resin | 4.80 | 15.50 | 30.28 | 34.34 | 36.37 | 37.76 |
| Cycle No. 5 without resin | 0.49 | 0.67 | 0.77 | 0.87 | 0.91 | 1.00 |

Example 2

Corn stover was pretreated using steam explosion at 200° C. for 5.4 min. Pretreated corn stover (PCS) 666 g with TS of 32.12% was mixed with 2 L aqueous washing solution (water to PCS weight ratio 3:1) and incubated with stirring for 30 minutes at room temperature. The used washing solution from the PCS was squeezed out through 8 layers cheese cloth and filtered through 32 layers cheese cloth. About 1800 ml used washing solution was obtained. The used washing solution was treated by incubation with 500 g of resin D380 and H103 (average used washing solution to resin ratio approximately 3:1) in a beaker for 60 minutes with shaking. D380 is a macroporous weakly basic anion exchanger, and H103 is macroporous non-polar resin. Prior to use the resin was washed in a conventional way. The treated washing solution was recycled to wash a new batch of 600 g unwashed PCS, followed by separation, filtration, and resin treatment and recycling for yet a washing. This washing solution was recycled 5 times to wash 5 batches of unwashed PCS. As control treatment used washing solution was recycled without resin treatment 5 times. Approximately 90% of the washing solution was recovered from each wash. The size of the subsequent PCS portion was correspondingly decreased to maintain constant water to PCS weight ratio.

The washed PCS was subjected to a fed-batch hydrolysis process starting with a batch hydrolysis comprising 50 g of water and substrate with an initial dry solids concentration of 12.60%. Penicillin was added for controlling bacterial contamination. Cellulase composition A was utilized for enzymatic hydrolysis in a concentration of 45 mg EP/g cellulose. Washed PCS was added in 3 additional loadings to a final weight of 300 grams and a final dry solids concentration of 30%. The fed-batch hydrolysis process was performed at 50° C. and pH 4.8. The samples at 72 hours, 96 hours and 120 hours are taken for sugar analysis. The results are shown in table 1.

The hydrolyzates were centrifuged and filtered by filter paper. The filtered hydrolyzate was pitched with dry yeast (0.5% w/w), 0.25% urea and fermented at 32° C. for 7 days. The results are shown in table 2.

TABLE 1

Hydrolysis of washed PCS using recycled water with and without D380 or H103 resin treatment. Glucose yield from cellulose (% of theoretical). Sampled after 72 hours, 96 hours and 120 hours of hydrolysis.

| | 72 hours | 96 hours | 120 hours |
|---|---|---|---|
| Cycle No. 1 | 63.63 | 72.29 | 74.84 |
| Cycle No 5 D380 | 60.31 | 72.03 | 76.11 |
| Cycle No 5 H103 | 62.39 | 70.45 | 70.88 |
| Cycle No 5 Non-Resin | 46.21 | 57.36 | 60.33 |

TABLE 2

Fermentation of hydrolyzates of PCS washed in recycled water with or without D380 or H103 resin treatment of wash water. Ethanol production (g/L) after fermentation for 7 days.

| | |
|---|---|
| Cycle No. 1 | 49.87 |
| Cycle No 5 D380 | 52.32 |
| Cycle No 5 H103 | 1.86 |
| Cycle No 5 Non-Resin | 1.33 |

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

The invention claimed is:

1. A process for converting a lignocellulose-containing material into a hydrolyzate comprising mono- and oligosaccharides, the method comprising the steps of:
   (a) subjecting a lignocellulose-containing material to a pretreatment;
   (b) washing the pretreated lignocellulose-containing material in an aqueous washing solution;
   (c) separating the pretreated and washed lignocellulose-containing material from the used washing solution, to obtain a pretreated and washed lignocellulose-containing material;

(d) removing an enzyme inhibitor and/or an inhibitor of a fermenting organism from the used aqueous washing solution obtained in step (c) by contacting the used aqueous washing solution obtained in step (c) with a column comprising a resin directly after washing and separating, and recycling the used aqueous washing solution with less enzyme inhibitor and/or less inhibitor of a fermenting organism to step (b);

(e) enzymatically hydrolyzing the separated lignocellulose-containing material obtained in step (c) resulting in at least partial hydrolysis of the cellulose and/or hemicellulose to obtain a hydrolyzate comprising mono- and/or oligosaccharides; and (f) continuously repeating steps (a) to (e).

2. The process of claim 1, wherein the lignocellulose-containing material originates from materials selected from the group consisting of: corn stover, corn fiber, hard wood, soft wood, cereal straw, switch grass, rice hulls, municipal solid waste, industrial organic waste, office paper, and mixtures thereof.

3. The process of claim 1, wherein the lignocellulose-containing material is chemically and/or mechanically pretreated in step (a).

4. The process of claim 1, wherein the lignocellulose-containing material is chemically pretreated in step (a), using an acid selected from the group consisting of sulphuric acid, acetic acid, citric acid, tartaric acid, and succinic acid, or mixtures thereof.

5. The process of claim 1, wherein the lignocellulose-containing material is mechanically pretreated in step (a) at a high temperature and/or a high pressure.

6. The process of claim 1, wherein the lignocellulose-containing material is subjected to hydrothermal pretreatment in step (a).

7. The process of claim 1, wherein the lignocellulose-containing material is subjected to hydrothermal pretreatment in step (a) comprising high pressure in the range from 300 to 600 psi.

8. The process of claim 1, wherein the lignocellulose-containing material is subjected to high temperature in step (a) in the range from about 100 to 300° C.

9. The process of claim 1, wherein the lignocellulose-containing material is pretreated in step (a) by steam explosion, dilute acid steam explosion and/or wet oxidation.

10. The process of claim 1, wherein the aqueous washing solution comprises a mixture of water and an organic solvent.

11. The process of claim 1, wherein the resin comprises $-NH_2$ as a functional group.

12. The process of claim 1, wherein the resin comprises $-SO_3$, $-COOH$, $-N+(CH_3)_3$, or $-N(CH_3)_2$ as a functional group.

13. The process of claim 1, wherein the enzyme inhibitor and/or the inhibitor of the fermenting organism is selected from the group consisting of terpenes, aldehyde, polyhydroxy aromatics, 4-OH benzyl alcohol, 4-OH benzaldehyde, 4-OH benzoic acid, trimethyl benzaldehyde, 2-furoic acid, coumaric acid, ferulic acid, phenol, guaiacol, veratrole, pyrogallollol, pyrogallol mono methyl ether, vanillyl alcohol, vanillin, isovanillin, vanillic acid, isovanillic acid, homovanillic acid, veratryl alcohol, veratraldehyd, veratric acid, 2-O-methyl gallic acid, syringyl alcohol, syringaldehyde, syringic acid, trimethyl gallic acid, homocatechol, ethyl vanillin, creosol, p-methyl anisol, anisaldehyde, anisic acid, furfural, hydroxymethylfurfural, 5-hydroxymethylfurfural, formic acid, acetic acid, levulinic acid, cinnamic acid, coniferyl aldehyde, isoeugenol, hydroquinone, and combinations thereof.

14. The process of claim 1, wherein the enzyme inhibitor and/or inhibitor of the fermenting organism is formic acid, acetic acid, or a combination thereof.

15. The process of claim 1, wherein hydrolysis is carried out using one or more hydrolases selected from the group consisting of cellulase, hemicellulase, amylase, protease, esterase, endoglucanase, beta-glucosidase, cellobiohydrolase, cellobiase, xylanase, alpha-amylase, alpha-glucosidase, glucoamylase, proteases and lipases, or a mixture thereof.

16. The process of claim 15, wherein the alpha-amylase is an acid amylase and/or a fungal alpha-amylase.

17. The process of claim 1, wherein hydrolysis is carried out at a temperature between 25° C. and 70° C.

18. The process of claim 1, wherein hydrolysis is carried out at a pH in the range from 3-8.

19. The process of claim 1, wherein hydrolysis is carried out for between 12 and 96 hours.

* * * * *